(12) United States Patent
Yamamoto

(10) Patent No.: US 11,062,442 B2
(45) Date of Patent: Jul. 13, 2021

(54) VASCULAR INFORMATION ACQUISITION DEVICE, ENDOSCOPE SYSTEM, AND VASCULAR INFORMATION ACQUISITION METHOD

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 97 days.

(21) Appl. No.: 16/124,202

(22) Filed: Sep. 7, 2018

(65) Prior Publication Data
US 2019/0005641 A1    Jan. 3, 2019

Related U.S. Application Data

(63) Continuation of application No. PCT/JP2016/085745, filed on Dec. 1, 2016.

(30) Foreign Application Priority Data

Mar. 8, 2016 (JP) .............................. JP2016-044070

(51) Int. Cl.
| | | |
|---|---|---|
| *G06T 7/00* | (2017.01) | |
| *A61B 1/04* | (2006.01) | |
| *A61B 5/02* | (2006.01) | |
| *A61B 5/145* | (2006.01) | |
| *A61B 5/026* | (2006.01) | |
| *A61B 5/024* | (2006.01) | |
| *A61B 1/00* | (2006.01) | |

(52) U.S. Cl.
CPC .............. *G06T 7/0012* (2013.01); *A61B 1/00* (2013.01); *A61B 1/00009* (2013.01); *A61B 1/04* (2013.01);
(Continued)

(58) Field of Classification Search
CPC ......... G06T 7/0012; G06T 2207/10028; G06T 2207/30104; G06T 2207/10068;
(Continued)

(56) References Cited

U.S. PATENT DOCUMENTS

2011/0237883 A1  9/2011 Chun
2011/0245642 A1  10/2011 Minetoma
(Continued)

FOREIGN PATENT DOCUMENTS

| CN | 102894948 A | * | 1/2013 | ......... A61B 1/00009 |
| EP | 3357404 | | 8/2018 | |

(Continued)

OTHER PUBLICATIONS

"Written Opinion of the International Searching Authority (Form PCT/ISA/237) of PCT/JP2016/085745," dated Mar. 7, 2017, with English translation thereof, pp. 1-6.

(Continued)

*Primary Examiner* — Amandeep Saini
(74) *Attorney, Agent, or Firm* — JCIPRNET

(57) ABSTRACT

There are provided a vascular information acquisition device, an endoscope system, and a vascular information acquisition method that can accurately acquire vascular information on a blood vessel of a target layer that is an object to be measured of a subject. A first blood vessel extraction unit (82) analyzes the image of a target layer to be measured and extracts a blood vessel (first blood vessel) from the image of a target layer. A blood vessel specification unit (84) specifies a blood vessel (second blood vessel) extending to a non-target layer from the target layer. In a case in which the second blood vessel is specified, a second blood vessel extraction unit (83) analyzes the image of the non-target layer in which the second blood vessel is present and extracts the specified second blood vessel from the image of the non-target layer.

10 Claims, 7 Drawing Sheets

(52) U.S. Cl.
CPC .............. *A61B 5/024* (2013.01); *A61B 5/026* (2013.01); *A61B 5/02007* (2013.01); *A61B 5/14542* (2013.01); *G06T 2207/10028* (2013.01); *G06T 2207/10068* (2013.01); *G06T 2207/30104* (2013.01)

(58) Field of Classification Search
CPC ......... A61B 1/00; A61B 1/00009; A61B 1/04; A61B 5/02007; A61B 5/14542; A61B 5/026; A61B 5/024
USPC ........................................................ 382/128
See application file for complete search history.

(56) References Cited

U.S. PATENT DOCUMENTS

2012/0197076 A1* 8/2012 Minetoma .......... A61B 1/00009
600/109
2014/0316283 A1 10/2014 Kaku et al.
2016/0038004 A1* 2/2016 Tanaka ................... A61B 34/10
600/371

FOREIGN PATENT DOCUMENTS

| JP | 2011087906 | 5/2011 | |
|---|---|---|---|
| JP | 2011200517 | 10/2011 | |
| JP | 2011217798 | 11/2011 | |
| JP | 2012152459 | 8/2012 | |
| WO | WO-2012147505 A1 * | 11/2012 | ............. G16H 30/40 |
| WO | 2015165989 | 11/2015 | |

OTHER PUBLICATIONS

"International Search Report (Form PCT/ISA/210) of PCT/JP2016/085745," dated Mar. 7, 2017, with English translation thereof, pp. 1-3.

"Search Report of Europe Counterpart Application", dated Feb. 15, 2019, p. 1-p. 7.

* cited by examiner

VASCULAR INFORMATION ACQUISITION DEVICE, ENDOSCOPE SYSTEM, AND VASCULAR INFORMATION ACQUISITION METHOD

CROSS-REFERENCE TO RELATED APPLICATIONS

This application is a Continuation of PCT International Application No. PCT/JP2016/085745 filed on Dec. 1, 2016, which claims priority under 35 U.S.C § 119(a) to Japanese Patent Application No. 2016-044070 filed on Mar. 8, 2016. Each of the above application(s) is hereby expressly incorporated by reference, in its entirety, into the present application.

BACKGROUND OF THE INVENTION

1. Field of the Invention

The present invention relates to a vascular information acquisition device, an endoscope system, and a vascular information acquisition method, and more particularly, to a technique that acquires accurate vascular information.

2. Description of the Related Art

Diagnosis using an endoscope system, which includes a light source device, an endoscope, and a processor device, is widely performed in the medical field. In the diagnosis using the endoscope system, an insertion part of the endoscope is inserted into a subject, an illumination light is applied from a distal end portion of the insertion part, and an object to be observed (a mucous membrane or the like present in the subject) irradiated with illumination light is imaged by an imaging unit mounted in the distal end portion of the endoscope. Then, the image of the object to be observed is generated using image signals, which are obtained from imaging, and is displayed on a monitor.

In the endoscope system, ordinarily, white illumination light (also referred to as normal light) is applied to image an object to be observed. Accordingly, an image from which the object to be observed can be observed with a natural tint (hereinafter, referred to as a "normal observation image") is displayed.

Further, an endoscope system, which obtains an image in which blood vessels to be observed, a pit pattern (pit structure), or the like is emphasized (hereinafter, referred to as a "special observation image") by using light having a specific wavelength range as illumination light, is also spread. Since information on blood vessels, a pit pattern, and the like is an important diagnostic material, the special observation image in which the blood vessels, the pit pattern, and the like are emphasized is particularly useful for diagnosis.

In the past, endoscope systems disclosed in JP2011-200517A and JP2011-087906A have been proposed as an endoscope system that acquires information on blood vessels.

JP2011-200517A discloses an endoscope system that uses a difference in a distance that light reaches caused by different wavelengths, images a plurality of layers having different depths by sequentially applying a plurality of pieces of light having different wavelength ranges, generates the oxygen saturation images of surface-layer blood vessels, middle layer blood vessels, and deep layer blood vessels from the images obtained from imaging, and simultaneously or independently displays these images on a monitor.

Further, JP2011-087906A discloses an endoscope system that generates a blood vessel image present between a surface layer and a depth of several mm-tenths on the basis of a normal observation image; puts indocyanine green into a body in advance; generates a blood vessel image present between the surface layer and a depth of several mm on the basis of a fluorescence image of indocyanine green that is taken through the irradiation of a subject with excitation light; generates a common blood vessel image, which is a portion common to both the blood vessel images, and a deep-portion blood vessel image that is a difference between both the blood vessel images; and displays the common blood vessel image and the deep-portion blood vessel image so that the common blood vessel image and the deep-portion blood vessel image can be identified.

SUMMARY OF THE INVENTION

There is a problem that accurate vascular information cannot be acquired in a case in which blood vessels extending to non-target layers from a target layer are present at the time of acquisition of vascular information necessary for the indexing of blood vessels of the target layer, which is a layer to be measured, among a plurality of layers, which have different depths, of a subject (vascular information, such as the lengths of blood vessels, the number of blood vessels, branches, sinuosity, or a travel pattern).

This problem will be described in detail with reference to FIG. 7. FIG. 7 is a schematic view showing blood vessels that are present in four layers (first to fourth layers $L_1$ to $L_4$), which have different depths, of a subject. Now, in a case in which a second layer $L_2$, which is adjacent to a first layer $L_1$ including a mucous membrane present in a subject, is set as a layer to be measured (hereinafter, referred to as a "target layer $L_2$"), a blood vessel 1 extending to a third layer $L_3$ (hereinafter, referred to as a "non-target layer $L_3$") and a fourth layer $L_4$ (hereinafter, referred to as a "non-target layer $L_4$"), which are positioned under the target layer $L_2$, from the target layer $L_2$ is shown by a thick line.

In a case in which vascular information on blood vessels of the target layer $L_2$ is to be acquired, blood vessels are extracted from only the image of the target layer $L_2$ as shown in FIG. 7 and vascular information on the extracted blood vessels is acquired. For this reason, in a case in which a blood vessel 1 extending to the non-target layers $L_3$ and $L_4$, which are positioned under the target layer $L_2$, from the target layer $L_2$ is present, only a portion, which is surrounded by a solid line, of the blood vessel 1 is extracted and a portion, which extends to the non-target layers $L_3$ and $L_4$ and is surrounded by a dotted line, of the blood vessel 1 is not extracted. Accordingly, there is a problem that real vascular information on the blood vessel 1 cannot be acquired.

The endoscope system disclosed in JP2011-200517A can individually acquire oxygen saturation information (vascular information) on the blood vessels of the respective layers having different depths or can acquire oxygen saturation information on blood vessels of a layer (target layer) having any depth, but does not extract blood vessels, which extend to non-target layers from a target layer, as the same blood vessels of the target layer and the non-target layers. For this reason, the endoscope system disclosed in JP2011-200517A has a problem that accurate vascular information cannot be acquired.

Further, in the endoscope system disclosed in JP2011-087906A, in a case in which a certain blood vessel extends to a deep portion from the surface layer, the blood vessel is displayed as the common blood vessel image and the deep-portion blood vessel image but a blood vessel present in only the deep portion is also extracted and displayed. Accordingly, the endoscope system disclosed in JP2011-087906A cannot extract the blood vessel extending to the deep portion from the surface layer. For this reason, the endoscope system disclosed in JP2011-087906A has a problem that accurate vascular information on a common blood vessel (surface-layer blood vessel) or a deep-portion blood vessel cannot be acquired.

The invention has been made in consideration of the above-mentioned circumstances, and an object of the invention is to provide a vascular information acquisition device, an endoscope system, and a vascular information acquisition method that can accurately acquire vascular information on blood vessels of a target layer to be measured of a plurality of layers, which have different depths, of a subject.

To achieve the object, a vascular information acquisition device according to an aspect of the invention comprises: an image acquisition unit that acquires images of a plurality of layers, which have different depths, of a subject; a target layer selector that selects one layer of the plurality of layers as a target layer; a first blood vessel extraction unit that analyzes the image of the selected target layer and extracts a first blood vessel from the image of the target layer; a blood vessel specification unit that specifies a second blood vessel extending to a non-target layer, which is a layer other than the target layer among the plurality of layers, from the selected target layer; and a second blood vessel extraction unit that analyzes the image of the non-target layer in which the specified second blood vessel is present and extracts the specified second blood vessel from the image of the non-target layer.

In a case in which a blood vessel extending to the non-target layers from the target layer is present at the time of acquisition of vascular information on blood vessels of a target layer to be measured of a subject, a problem that accurate vascular information cannot be acquired is found.

According to the aspect of the invention, the image of the target layer to be measured is analyzed and the blood vessel (first blood vessel) is extracted from the image of the target layer. However, in a case in which the blood vessel (second blood vessel) extending to the non-target layers from the target layer is further specified and the second blood vessel is specified, the images of the non-target layers in which the second blood vessel is present are analyzed and the specified second blood vessel is extracted from the images of the non-target layers. In a case in which the blood vessel extending to the non-target layers from the target layer is present as described above, the blood vessel (second blood vessel) of the non-target layers, which extends to the non-target layers from the target layer, is also extracted in addition to the blood vessel (first blood vessel) of the target layer. Accordingly, vascular information on the blood vessel of the target layer can be accurately acquired.

According to another aspect of the invention, it is preferable that the vascular information acquisition device further comprises a vascular information calculation unit calculating vascular information on the first and second blood vessels extracted by the first blood vessel extraction unit and the second blood vessel extraction unit. Accordingly, vascular information on the target layer can be accurately calculated.

According to another aspect of the invention, it is preferable that the vascular information acquisition device further comprises a display control unit allowing a display unit to display the first and second blood vessels extracted by the first blood vessel extraction unit and the second blood vessel extraction unit. In this case, one image in which the first blood vessel and the second blood vessel are combined with each other may be displayed, or a stereoscopic image including the first blood vessel of the target layer and the second blood vessel of the non-target layers may be displayed.

According to another aspect of the invention, in the vascular information acquisition device, it is preferable that, in a case in which the second blood vessel also extends to a non-target layer different from the non-target layer, the second blood vessel extraction unit also performs the extraction of the second blood vessel on the different non-target layer. Accordingly, in a case in which the second blood vessel extends over a plurality of non-target layers, the second blood vessel can be sequentially traced and extracted.

According to another aspect of the invention, in the vascular information acquisition device, it is preferable that the second blood vessel extraction unit stops the extraction of the second blood vessel, which extends to the non-target layer, on the basis of a determination value.

According to another aspect of the invention, in the vascular information acquisition device, it is preferable that the determination value is information determined so as to correspond to the vascular information on the second blood vessel and the second blood vessel extraction unit determines whether to continue or stop the extraction of the second blood vessel according to whether or not the vascular information on the second blood vessel satisfies the determined information. The determination value is information corresponding to vascular information on the second blood vessel, such as the branches and thickness of the second blood vessel, and the second blood vessel extraction unit can stop the extraction of the second blood vessel in a case in which, for example, the second blood vessel is branched.

According to another aspect of the invention, in the vascular information acquisition device, it is preferable that the determination value is depth information corresponding to a depth of a blood vessel and the second blood vessel extraction unit stops the extraction of the second blood vessel in a case in which a depth of the second blood vessel reaches a depth indicated by the depth information.

According to another aspect of the invention, in the vascular information acquisition device, it is preferable that the vascular information calculation unit calculates a plurality of pieces of vascular information including at least two of the number of blood vessels, the number of branches of blood vessels, thickness and length of a blood vessel, an interval between blood vessels, depth, sinuosity, area, and density of a blood vessel, concentration of blood in a blood vessel, an oxygen saturation of a blood vessel, a ratio of arteries, a ratio of veins, a travel pattern of blood vessels, or a blood flow rate in a blood vessel.

An endoscope system according to another aspect of the invention comprises: the above-mentioned vascular information acquisition device; an image-acquisition-condition setting unit that includes a plurality of image acquisition conditions corresponding to the taking of images of a plurality of layers, which have different depths, of a subject, and sets any image acquisition condition of the plurality of image acquisition conditions; and an endoscope that images the subject under the image acquisition condition set by the image-acquisition-condition setting unit and acquires an image of a layer, which has a depth corresponding to the set image acquisition condition, among the plurality of layers.

The image acquisition unit acquires images of the plurality of layers, which have different depths, of the subject from the endoscope. The image acquisition condition includes a condition, such as the wavelength of a light source illuminating the subject or the type of the light source, and the endoscope can acquire the image of a layer, which has a depth corresponding to the image acquisition condition, by imaging the subject under the set image acquisition condition.

According to another aspect of the invention, in the endoscope system, it is preferable that the image-acquisition-condition setting unit sequentially selects one image acquisition condition among the plurality of image acquisition conditions and sets the selected image acquisition condition, and the endoscope images the subject whenever the image acquisition condition is set by the image-acquisition-condition setting unit and sequentially acquires an image of a layer, which has a depth corresponding to the set image acquisition condition. According to this, after the images of the plurality of layers, which have different depths, of the subject are acquired in advance regardless of whether or not the second blood vessel is specified by the blood vessel specification unit, the image of a layer (target layer), which is selected among the acquired images of the plurality of layers, is analyzed and the first blood vessel is extracted. In a case in which the second blood vessel extending to the non-target layers from the target layer is specified, the images of the non-target layers are analyzed and the second blood vessel of the non-target layers is extracted.

According to another aspect of the invention, in the endoscope system, the image-acquisition-condition setting unit sets an image acquisition condition corresponding to an image of the selected target layer in a case in which the target layer is selected by the target layer selector, and sets an image acquisition condition corresponding to an image of a non-target layer adjacent to the target layer in a case in which the second blood vessel is specified by the blood vessel specification unit, and the endoscope images the subject whenever the image acquisition condition is set by the image-acquisition-condition setting unit, and acquires an image of a layer, which has a depth corresponding to the set image acquisition condition. According to this, in a case in which the image of the selected target layer is acquired, the acquired image of the target layer is analyzed, the first blood vessel is extracted, and the second blood vessel extending to the non-target layers from the target layer is specified, the image acquisition condition is switched to take the images of the non-target layers, the taken images of the non-target layers are analyzed, and the second blood vessel of the non-target layers is extracted.

A vascular information acquisition method according to another aspect of the invention comprises: a step of acquiring images of a plurality of layers, which have different depths, of a subject; a step of selecting one layer of the plurality of layers as a target layer; a step of analyzing an image of the selected target layer and extracting a first blood vessel from the image of the target layer; a step of specifying a second blood vessel extending to a non-target layer, which is a layer other than the target layer among the plurality of layers, from the selected target layer; and a step of analyzing the image of the non-target layer in which the specified second blood vessel is present and extracting the specified second blood vessel from the image of the non-target layer.

According to another aspect of the invention, it is preferable that the vascular information acquisition method further comprises a step of calculating vascular information on the extracted first and second blood vessels.

According to another aspect of the invention, in the vascular information acquisition method, it is preferable that a plurality of pieces of vascular information including at least two of the number of blood vessels, the number of branches of blood vessels, thickness and length of a blood vessel, an interval between blood vessels, a depth of a blood vessel based on a mucous membrane, sinuosity, area, and density of a blood vessel, concentration of blood in a blood vessel, an oxygen saturation of a blood vessel, a ratio of arteries, a ratio of veins, a travel pattern of blood vessels, or a blood flow rate in a blood vessel are calculated in the step of calculating the vascular information.

According to the invention, in a case in which a blood vessel extending to non-target layers from a target layer to be measured of a subject is present, a blood vessel (second blood vessel) of the non-target layers, which extends to the non-target layers from the target layer, is also extracted in addition to a blood vessel (first blood vessel) of the target layer. Accordingly, vascular information on the blood vessel of the target layer can be accurately acquired.

DESCRIPTION OF THE PREFERRED EMBODIMENTS

Embodiments of a vascular information acquisition device, an endoscope system, and a vascular information acquisition method according to the invention will be described below with reference to the accompanying drawings.

[Entire Configuration of Endoscope System]

Figure 1:
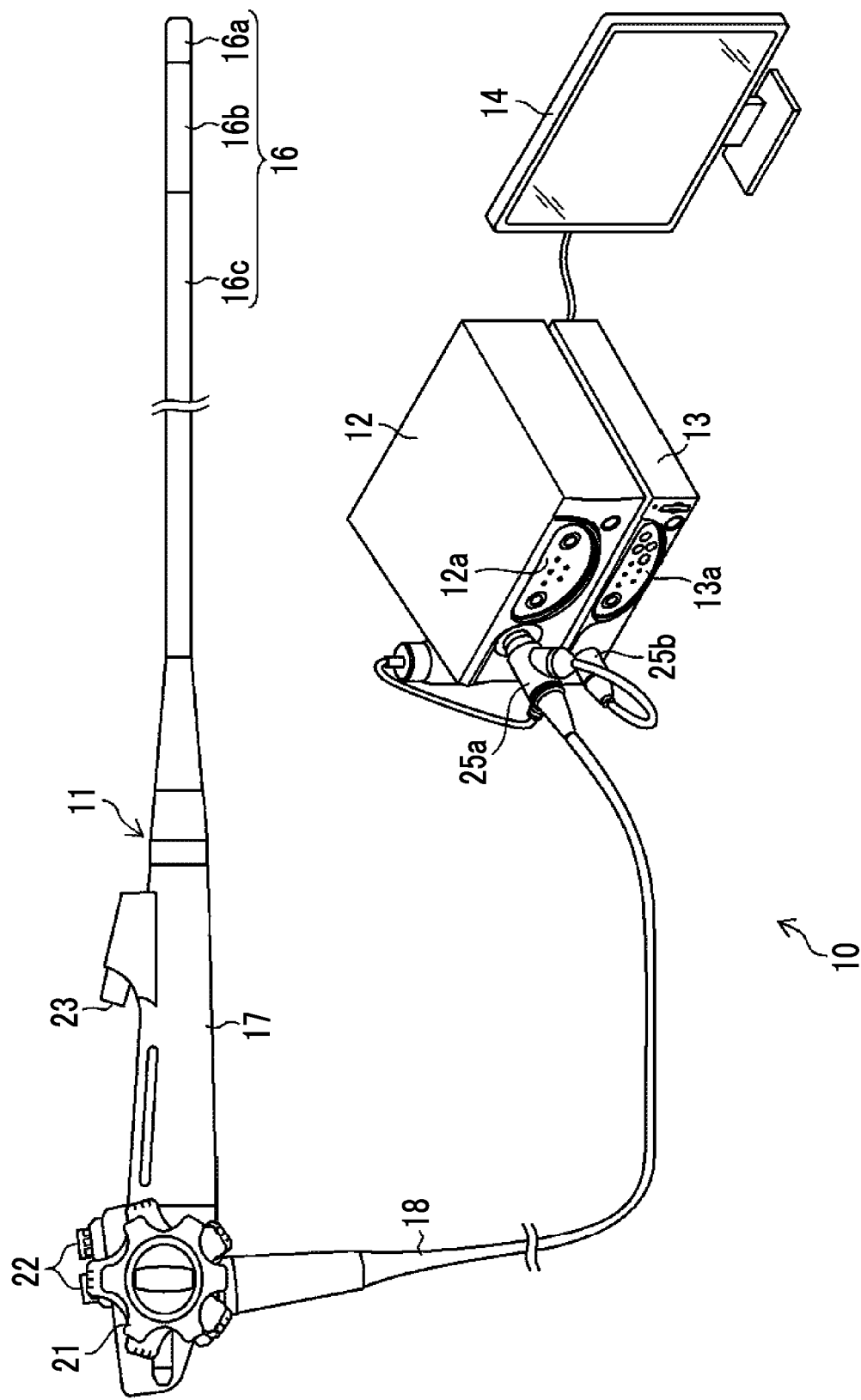
FIG. 1 is a perspective view of an endoscope system according to the invention.

FIG. 1 is a perspective view showing the appearance of an endoscope system 10 according to the invention.

As shown in FIG. 1, the endoscope system 10 mainly includes an endoscope 11 as an electronic scope (here, a flexible endoscope) that images an object to be observed in a subject, a light source device 12, a processor device 13, and a display unit 14, such as a liquid crystal monitor.

The light source device 12 supplies various kinds of illumination light, such as white light that is used to take a normal observation image and light having a specific wavelength range that is used to take a special observation image, to the endoscope 11. The processor device 13 corresponds to one form of the vascular information acquisition device according to the invention; and has a function to generate image data of a normal observation image and/or a special observation image for display or recording on the basis of image signals obtained by the endoscope 11 and a function to analyze a special observation image (in this embodiment, an image showing structures (blood vessels) of a subject or an image facilitating seeing blood vessels) to acquire vascular information, such as the number of blood vessels, the number of branches of blood vessels, and the thicknesses of blood vessels.

The display unit 14 displays the normal observation image or the special observation image of an object to be observed on the basis of image data input from the processor device 13.

The endoscope 11 includes a flexible insertion part 16 that is to be inserted into a subject, a hand operation unit 17 that is connected to the proximal end portion of the insertion part 16 and is used for the grip of the endoscope 11 and the operation of the insertion part 16, and a universal cord 18 that connects the hand operation unit 17 to the light source device 12 and the processor device 13.

Figure 2:
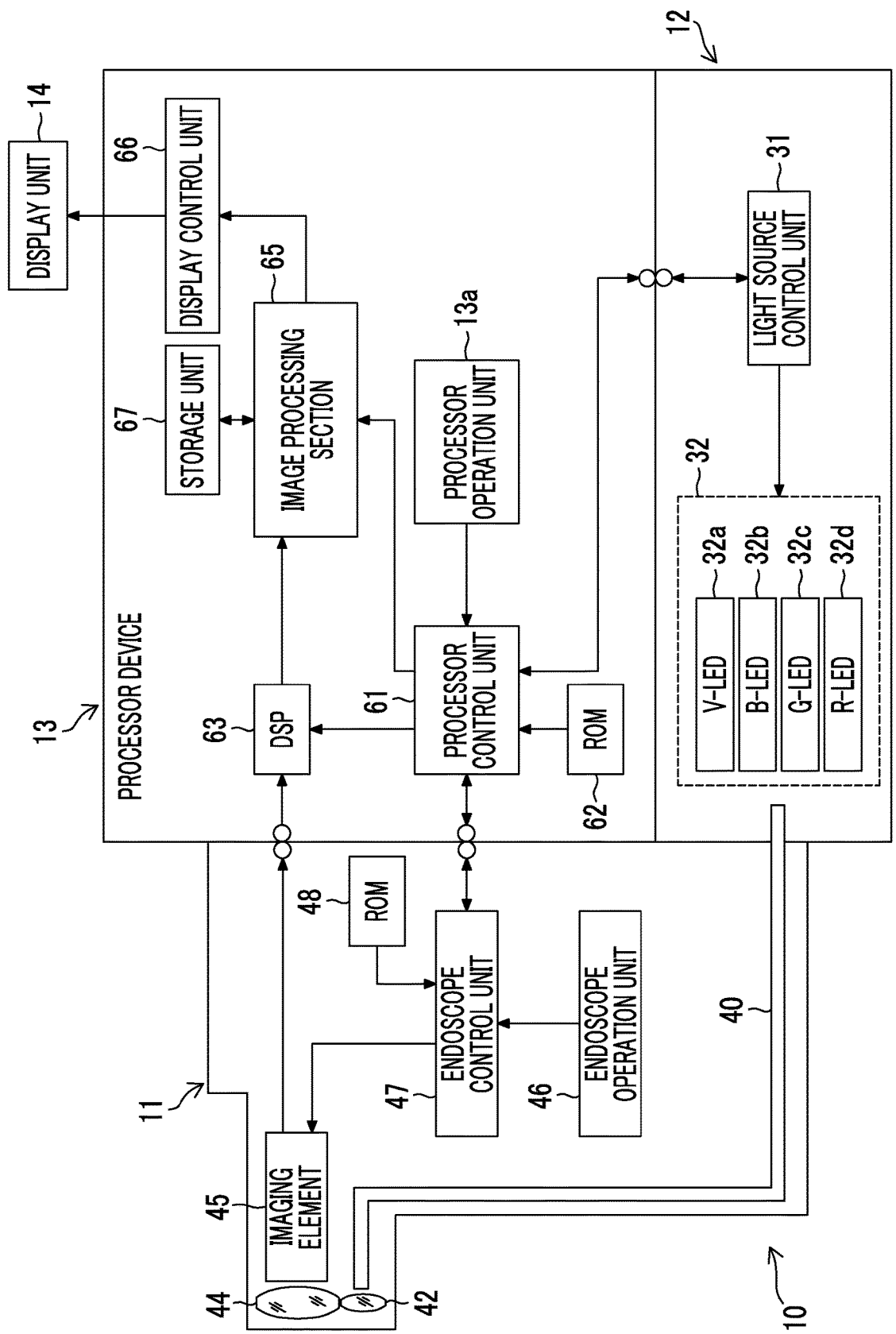
FIG. 2 is a block diagram showing the electrical configuration of the endoscope system.

An illumination lens 42, an objective lens 44, an imaging element 45, and the like are built in an insertion-part-distal end portion 16a that is a distal end portion of the insertion part 16 (see FIG. 2). A bendable portion 16b is connected to the rear end of the insertion-part-distal end portion 16a. Further, a flexible tube portion 16c is connected to the rear end of the bendable portion 16b.

The hand operation unit 17 is provided with an angle knob 21, operation buttons 22, a forceps inlet 23, and the like. The angle knob 21 is operated to rotate in a case in which the bending direction and the bending angle of the bendable portion 16b are to be adjusted. The operation buttons 22 are used for various operations, such as the supply of air, the supply of water, and suction. The forceps inlet 23 communicates with a forceps channel formed in the insertion part 16. Further, the hand operation unit 17 is provided with an endoscope operation unit 46 (see FIG. 2) that includes a static image pickup button (not shown) and a mode switch used to switch a normal observation mode and a special observation mode, and the like.

An air supply/water supply channel, a signal cable, a light guide, and the like are built in the universal cord 18. A connector part 25a that is to be connected to the light source device 12 and a connector part 25b that is to be connected to the processor device 13 are provided at the distal end portion of the universal cord 18. Accordingly, illumination light is supplied to the endoscope 11 from the light source device 12 through the connector part 25a, and image signals obtained by the endoscope 11 are input to the processor device 13 through the connector part 25b.

A light source operation unit 12a that includes a power button, a lighting button used to turn on a light source, a brightness adjustment button, and the like is provided on the front surface of the light source device 12, and a processor operation unit 13a that includes a power button, a target layer selector selecting one layer of a plurality of layers, which have different depths, of a subject as a target layer, and the like is provided on the front surface of the processor device 13.

[Electrical Configuration of Endoscope System]

FIG. 2 is a block diagram showing the electrical configuration of the endoscope system 10.

As shown in FIG. 2, the light source device 12 includes a light source control unit 31 and a light source unit 32. The light source control unit 31 controls the light source unit 32 and communicates with a processor control unit 61 of the processor device 13 to exchange various kinds of information.

The light source unit 32 includes, for example, a plurality of semiconductor light sources. In this embodiment, the light source unit 32 includes four color LEDs, that is, a violet light emitting diode (V-LED) 32a, a blue light emitting diode (B-LED) 32b, a green light emitting diode (G-LED) 32c, and a red light emitting diode (R-LED) 32d. The V-LED 32a is a violet light source that emits violet light of which a central wavelength is 405 nm and a wavelength range is in the range of 380 to 420 nm. The B-LED 32b is a blue semiconductor light source that emits blue light of which a central wavelength is 460 nm and a wavelength range is in the range of 420 to 500 nm. The G-LED 32c is a green semiconductor light source that emits green light of which a wavelength range is in the range of 480 to 600 nm. The R-LED 32d is a red semiconductor light source that emits red light of which a central wavelength is in the range of 620 to 630 nm and a wavelength range is in the range of 600 to 650 nm. The central wavelength of each of the V-LED 32a and the B-LED 32b has a width in the range of about ±5 nm to ±10 nm.

The turn-on/off of each of the respective LEDs 32a to 32d, the amount of light emitted from each of the LEDs 32a to 32d during the turn-on of each of the LEDs 32a to 32d, and the like can be controlled according to the input of an independent control signal to each LED from the light source control unit 31. In the case of the normal observation mode, the light source control unit 31 turns on all of the V-LED 32a, the B-LED 32b, the G-LED 32c, and the R-LED 32d. For this reason, white light including violet light, blue light, green light, and red light is used as illumination light in the normal observation mode.

On the other hand, in the case of the special observation mode, the light source control unit 31 turns on any one light source of the V-LED 32a, the B-LED 32b, the G-LED 32c, and the R-LED 32d or a plurality of appropriately combined light sources. Alternatively, in a case in which the light source control unit 31 turns on a plurality of light sources, the light source control unit 31 controls the amount of light emitted from each light source (the light amount ratio of each light source). Accordingly, the light source control unit 31 enables the images of a plurality of layers, which have different depths, of a subject to be taken.

Each color light emitted from each of the LEDs 32a to 32d is incident on a light guide 40, which is inserted into the endoscope 11, through an optical path connecting part, which is formed of a mirror, a lens, or the like, and a stop mechanism (not shown).

The endoscope 11 mainly includes the light guide 40, the illumination lens 42, the objective lens 44, the imaging element 45, the endoscope operation unit 46, an endoscope control unit 47, and a read-only memory (ROM) 48.

A large-diameter optical fiber, a bundled fiber, or the like is used as the light guide 40. The incident end of the light guide 40 is inserted into the light source device 12 through the connector part 25a, and the emission end of the light guide 40 passes through the insertion part 16 and faces the illumination lens 42 provided in the insertion-part-distal end portion 16a. Illumination light, which is supplied to the light guide 40 from the light source device 12, is applied to an object to be observed through the illumination lens 42. Then, illumination light, which is reflected and/or scattered by the object to be observed, is incident on the objective lens 44.

The objective lens 44 forms an image on the imaging surface of the imaging element 45 with reflected light or scattered light of the incident illumination light (that is, the optical image of the object to be observed).

The imaging element 45 is a complementary metal oxide semiconductor (CMOS) imaging element or a charge coupled device (CCD) imaging element, and is positioned relative to the objective lens 44 and is fixed at a position on the back side of the objective lens 44. A plurality of pixels, which are formed of a plurality of photoelectric conversion elements (photodiodes) photoelectrically converting an optical image, are two-dimensionally arrayed on the imaging surface of the imaging element 45. Further, red (R), green (G), and blue (B) color filters are disposed for every pixel on the incident sides of the plurality of pixels of the imaging element 45 of this embodiment, so that R pixels, G pixels, and B pixels are formed. The filter array of the RGB color filters is generally Bayer array, but is not limited thereto.

The imaging element 45 converts the optical image, which is formed by the objective lens 44, into electrical image signals and outputs the electrical image signals to the processor device 13.

Since an analog/digital (A/D) converter is built in the imaging element 45 in a case in which the imaging element 45 is a CMOS imaging element, digital image signals are directly output to the processor device 13 from the imaging element 45. Further, in a case in which the imaging element 45 is a CCD imaging element, image signals output from the imaging element 45 are converted into digital image signals by an A/D converter (not shown) or the like and the digital image signals are then output to the processor device 13.

The endoscope operation unit 46 is an operation unit that includes the static image pickup button and the mode switch used to switch the normal observation mode and the special observation mode, and the like.

The endoscope control unit 47 sequentially executes various programs and data that are read from the ROM 48 or the like according to the operation of the endoscope operation unit 46, and mainly controls the drive of the imaging element 45. For example, the endoscope control unit 47 controls the imaging element 45 so as to read signals of the R pixels, the G pixels, and the B pixels of the imaging element 45 in the case of the normal observation mode, and controls the imaging element 45 so as to read only signals of the B pixels of the imaging element 45 having spectral sensitivity in the wavelength range of violet light and the wavelength range of blue light in a case in which violet light is emitted from the V-LED 32a or blue light is emitted from the B-LED 32b as illumination light in the special observation mode.

Further, the endoscope control unit 47 communicates with the processor control unit 61 of the processor device 13 to transmit information on the operation of the endoscope operation unit 46, identification information that is stored in the ROM 48 and is used to identify the type of the endoscope 11, and the like to the processor device 13.

The processor device 13 includes the processor operation unit 13a, the processor control unit 61, a ROM 62, a digital signal processor (DSP) 63, an image processing section 65, a display control unit 66, a storage unit 67, and the like.

The processor operation unit 13a includes a power button, a target layer selector selecting one layer of a plurality of layers, which have different depths, of the subject as a target layer, and the like.

The processor control unit 61 controls the respective components of the processor device 13 and controls the light source device 12 by reading necessary programs and data from the ROM 62 according to information on the operation of the processor operation unit 13a and information on the operation of the endoscope operation unit 46, which is received through the endoscope control unit 47, and sequentially processing the necessary programs and data. The processor control unit 61 communicates with the endoscope control unit 47 and receives information on the operation of the endoscope operation unit 46 (for example, information representing the normal observation mode or the special observation mode switched by the switching operation of the mode switch, and the like). However, the processor operation unit 13a may be provided with a mode switch and the processor control unit 61 may be adapted to receive the operation of the mode switch of the processor operation unit 13a. Alternatively, the processor control unit 61 may be adapted to receive a necessary instruction input from another external device, such as a keyboard, connected through an interface (not shown).

The DSP 63, which functions as one form of an image acquisition unit for acquiring image data output from the endoscope 11 (imaging element 45), performs various kinds of signal processing, such as defect correction processing, offset processing, white balance correction, gamma correction, and demosaicing, on image data, which is input from the endoscope 11 and corresponds to one frame, under the control of the processor control unit 61 to generate image data corresponding to one frame.

The image data is input to the image processing section 65 from the DSP 36, and the image processing section 65 performs image processing, such as color conversion processing, color emphasis processing, and structure emphasis processing, on the input image data as necessary to generate image data representing an endoscope image of the object to be observed. The color conversion processing is processing for performing color conversion on the image data by 3×3 matrix processing, gradation conversion processing, three-dimensional look-up table processing, and the like. The color emphasis processing is processing for emphasizing a color on the image data having been subjected to the color conversion processing so that a difference in tint occurs between, for example, a blood vessel and a mucous membrane. The structure emphasis processing is processing for emphasizing a specific tissue or structure included in an object to be observed, such as blood vessels or a pit pattern, and is performed on image data having been subjected to the color emphasis processing.

Further, the image processing section 65 can read required image data from the storage unit 67 in which the image data input from the DSP 63 is stored, and can also perform the above-mentioned image processing on the read image data. The storage unit 67 may be a built-in memory, and may be a memory card that is detachably mounted on the processor device 13.

Figure 3:
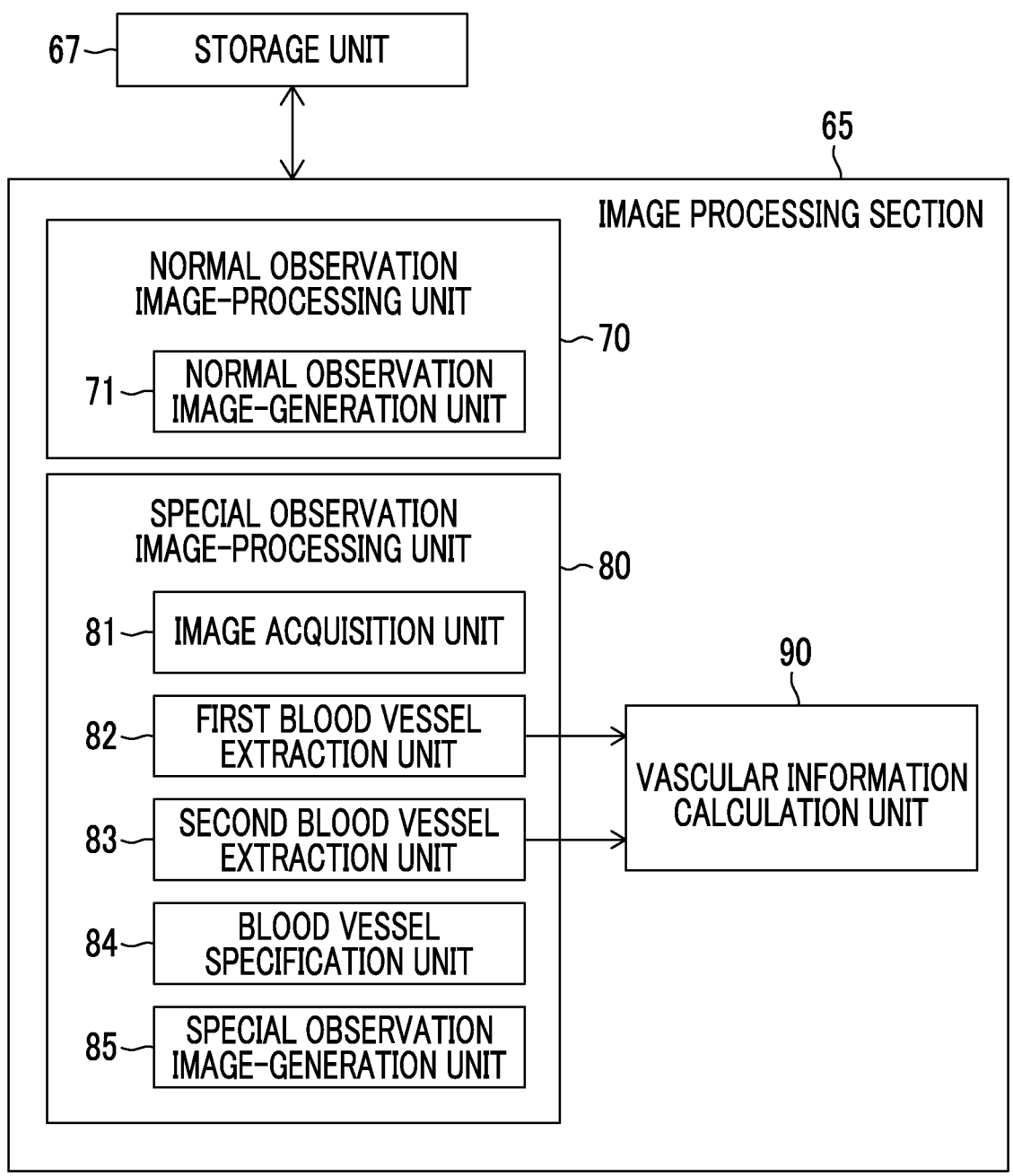
FIG. 3 is a functional block diagram showing the detailed configuration of main components of an image processing section 65 shown in FIG. 2.

FIG. 3 is a functional block diagram showing the detailed configuration of main components of the image processing section 65 shown in FIG. 2.

As shown in FIG. 3, the image processing section 65 mainly includes a normal observation image-processing unit 70, a special observation image-processing unit 80, and a vascular information calculation unit 90.

Since the image data representing the endoscope image generated by the image processing section 65 is the image data representing the normal observation image in a case in which an observation mode is the normal observation mode and is the image data representing the special observation image in a case in which an observation mode is the special observation mode, the contents of the color conversion processing, the color emphasis processing, and the structure emphasis processing vary depending on the observation mode.

That is, information representing an observation mode is added to the image processing section 65 from the processor control unit 61. In a case in which an observation mode is the normal observation mode, image data taken under image acquisition conditions of the normal observation mode is input to the normal observation image-processing unit 70 (normal observation image-generation unit 71) of the image processing section 65 and the normal observation image-processing unit 70 generates image data representing the normal observation image by performing the above-mentioned various kinds of signal processing on the input image data so that an object to be observed has a natural tint.

On the other hand, in a case in which an observation mode is the special observation mode, image data taken under image acquisition conditions of the special observation mode is input to the special observation image-processing unit 80 of the image processing section 65 and the special observation image-processing unit 80 generates the image data representing the special observation image by performing the above-mentioned various kinds of signal processing for emphasizing the structure (blood vessel) of the object to be observed on the input image data.

Further, the special observation image-processing unit 80 includes an image acquisition unit 81, a first blood vessel extraction unit 82, a second blood vessel extraction unit 83, a blood vessel specification unit 84, and a special observation image-generation unit 85. The special observation image-generation unit 85 is a unit that generates the image data representing the special observation image, and generates, for example, image data representing a special observation image in which the mucous membrane of a subject is set to a pink color, a blood vessel present at a relatively shallow position in an object to be observed on the basis of the surface of the mucous membrane (a so-called surface-layer blood vessel) is set to a magenta color (for example, a brown color), a blood vessel present at a relatively deep position in the object to be observed on the basis of the surface of the mucous membrane (a so-called middle-deep-layer blood vessel) is set to a cyan color (for example, a green color), and the blood vessel of the object to be observed is emphasized by a difference in color with respect to the mucous membrane expressed by a pink color.

<Vascular Information Acquisition Device>

Next, an embodiment of the vascular information acquisition device according to the invention will be described.

The light source device 12 and the processor device 13 correspond to one form of the vascular information acquisition device according to the invention, acquire the images of a plurality of layers, which have different depths, of the subject and acquire vascular information necessary for the indexing of blood vessels included in a target layer that is a layer to be measured among the plurality of layers (vascular information, such as the lengths of blood vessels, the number of blood vessels, branches, sinuosity, or a travel pattern). Hereinafter, a mode in which the vascular information necessary for the indexing of the blood vessels of the target layer (vascular information of the target layer) is acquired is referred to as a "vascular information acquisition mode" as an aspect of the special observation mode.

The plurality of layers, which have different depths, of the subject can be classified into, for example, a "surface layer", a "middle layer", and a "deep layer". For example, the depth of the "surface layer" from the surface of the mucous membrane is in the range of about 0 to 50 μm, the depth of the "middle layer" from the surface of the mucous membrane is in the range of about 50 to 200 μm, and the depth of the "deep layer" from the surface of the mucous membrane is in the range of about 200 to 500 μm. Further, a "middle-deep layer" is in a range matching with the middle layer and the deep layer, and the depth of the "middle-deep layer" from the surface of the mucous membrane is in the range of about 50 to 500 μm. Of course, the range of the depth of each of these layers is exemplary, and the depth from the surface of the mucous membrane may be classified into depths of four or more layers.

Figure 7:
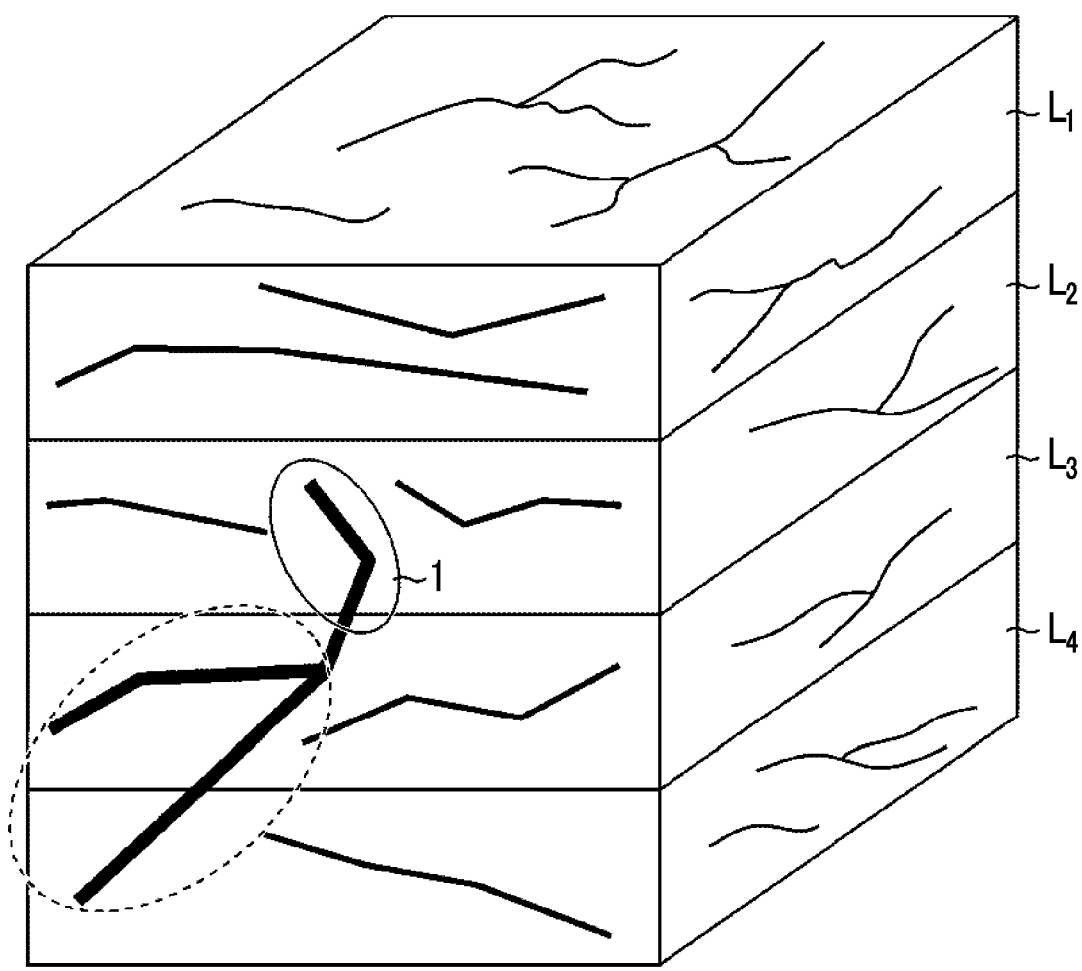
FIG. 7 is a schematic view showing blood vessels that are present in four layers, which have different depths, of a subject.

In this embodiment, the depth from the surface of the mucous membrane is classified into depths of four layers (first to fourth layers $L_1$ to $L_4$) as shown in FIG. 7 and it is possible to take the images of the first to fourth layers $L_1$ to $L_4$ by setting image acquisition conditions, such as the type of illumination light emitted from the light source unit 32 of the light source device 12 and the control of the drive of the imaging element 45 according to the type of the illumination light. The first to fourth layers $L_1$ to $L_4$ having different depths are not limited to a case in which there is no overlapping portion between the layers as shown in FIG. 7, and the adjacent layers may partially overlap each other.

The processor control unit 61 has a function as an image-acquisition-condition setting unit for setting any one image acquisition condition among the plurality of image acquisition conditions, wherein the plurality of image acquisition conditions corresponds to the taking of the images of the plurality of layers (first to fourth layers $L_1$ to $L_4$), which have different depths, of the subject, and allows the images of the plurality of layers to be taken by controlling the light source device 12 and the endoscope 11 according to the image acquisition conditions corresponding to layers to be imaged.

Further, the processor operation unit 13a includes a target layer selector, which selects one layer of the first to fourth layers $L_1$ to $L_4$ as a target layer. The target layer, which is selected by the target layer selector, is a layer to be measured from which vascular information is to be measured.

In a first embodiment of the vascular information acquisition device, in a case in which the vascular information acquisition mode is set (for example, a case in which an observation mode is the special observation mode and the target layer is selected by the target layer selector or a case in which the vascular information acquisition mode is set by the processor operation unit 13a), the processor control unit 61 sequentially sets the image acquisition conditions corresponding to the taking of the images of the first to fourth layers $L_1$ to $L_4$ and sequentially takes the images of all of the first to fourth layers $L_1$ to $L_4$.

In FIG. 3, the processor control unit 61 or the image processing section 65 store image data, which represent the images of all of the first to fourth layers $L_1$ to $L_4$ taken in this way, in the storage unit 67. The image data, which represent the images of all of the first to fourth layers $L_1$ to $L_4$, may be stored in a buffer memory (not shown) provided in the image processing section 65, or the like.

In a case in which the target layer is selected by the target layer selector of the processor operation unit 13a, the processor control unit 61 outputs information representing the selected target layer to the image processing section 65. In a case in which the information representing the target layer is input to the image processing section 65 from the processor control unit 61, the image processing section 65 reads the image data of the target layer among the image data of the first to fourth layers $L_1$ to $L_4$, which are stored in the storage unit 67, from the storage unit 67 first.

The first blood vessel extraction unit 82 analyzes the image of the target layer on the basis of the read image data of the target layer, and extracts blood vessels (first blood vessels) from the image of the target layer. It is thought that the extraction of the blood vessel is performed by frequency filtering processing. Since a spatial frequency in an image tends to be increased as the blood vessel becomes thin, a thin surface-layer blood vessel can be extracted in a case in which high-frequency filtering processing is performed and a thick blood vessel can be extracted in a case in which low-frequency filtering processing to medium-frequency filtering processing is performed. In this embodiment, all blood vessels present in the target layer are extracted regardless of the thickness of a blood vessel. Further, a method of extracting a blood vessel is not limited to filtering processing.

Figure 4:
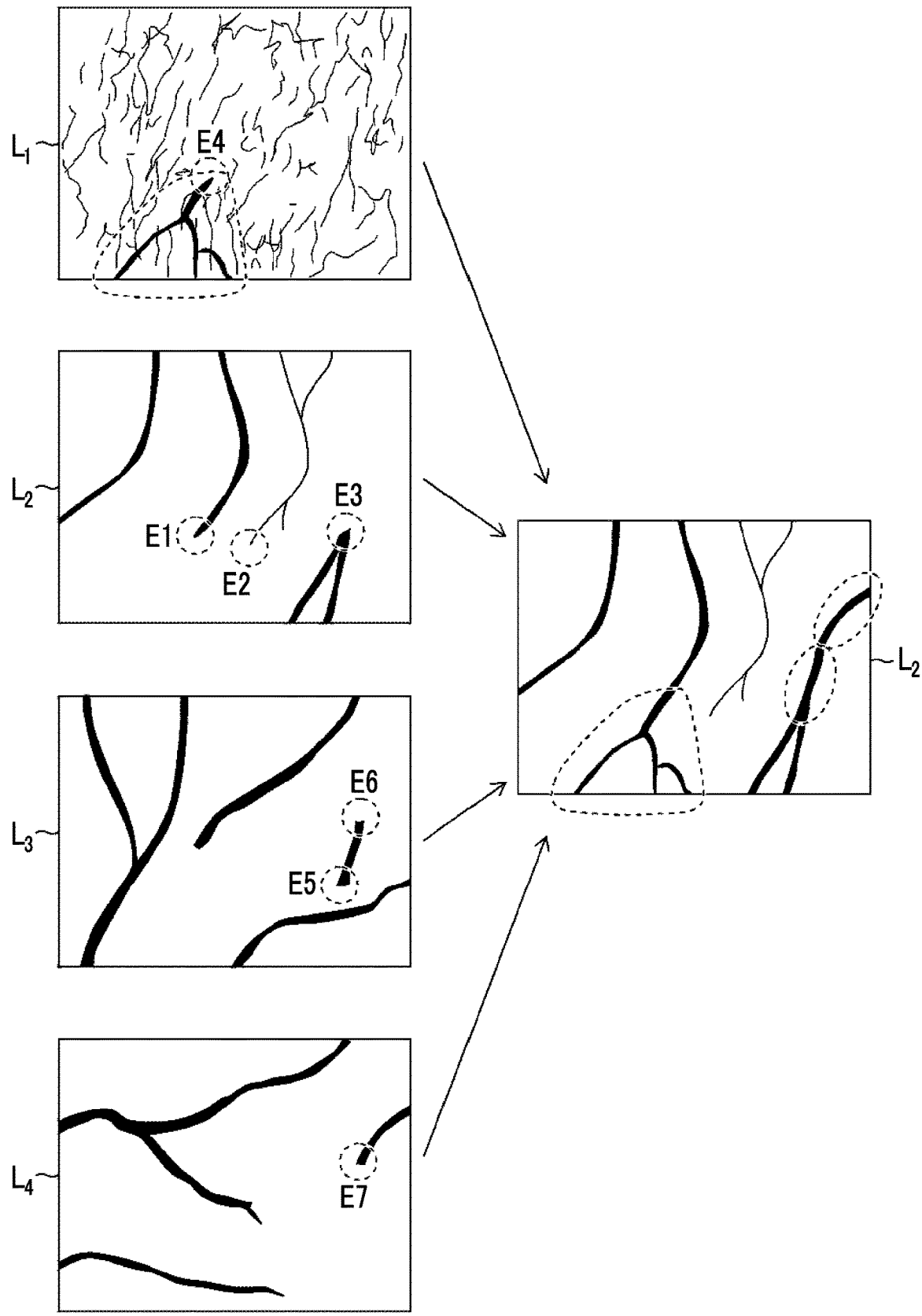
FIG. 4 is a diagram showing an example of a blood vessel that is extracted from four layers.

FIG. 4 shows an example of a blood vessel that is extracted from the four layers (first to fourth layers $L_1$ to $L_4$).

The blood vessel specification unit 84 specifies blood vessels (second blood vessels) that extend to non-target layers (layers other than the target layer among a plurality of layers) from the target layer among the first blood vessels extracted by the first blood vessel extraction unit 82.

Now, in a case in which the second layer $L_2$ adjacent to the first layer $L_1$ including a mucous membrane present in a subject among the first to fourth layers $L_1$ to $L_4$ is set as a layer to be measured (hereinafter, referred to as a "target layer $L_2$") as shown in FIG. 4, the blood vessel specification unit 84 extracts blood vessels, which are cut in the image, among the first blood vessels of the target layer $L_2$ as the second blood vessels that extend to the non-target layers from the target layer $L_2$.

In the example shown in FIG. 4, the blood vessel specification unit 84 specifies the cut second blood vessels and detects the characteristics (positions, thicknesses, and directions in the image) of end points E1, E2, and E3 of the cut second blood vessels. The extraction of the end points of the cut second blood vessels can be performed using a publicly known technique, such as thinning processing or an edge filter.

In a case in which the second blood vessels are specified by the blood vessel specification unit 84, the image acquisition unit 81 reads the image data of the non-target layers, which are adjacent to the target layer and are positioned on and beneath the target layer, (in this embodiment, the first and third layers $L_1$ and $L_3$) from the storage unit 67.

The second blood vessel extraction unit 83 extracts the second blood vessels, which extend from the target layer $L_2$, among blood vessels of the read non-target layers (hereinafter, the first layer $L_1$ positioned on the target layer $L_2$ is referred to as a "non-target layer $L_1$" and the third layer $L_3$ positioned beneath the target layer $L_2$ is referred to as a "non-target layer $L_3$"). In the extraction of the second blood vessels performed by the second blood vessel extraction unit 83, blood vessels, which are cut in the image, among the blood vessels of the non-target layers $L_1$ and $L_3$, and have the characteristics of end points having the same positions, thicknesses, and directions as those of the end points E1, E2, and E3 of the second blood vessels of the target layer $L_2$ in the image, are extracted.

Since the characteristics of the end point E1 of the second blood vessel of the target layer $L_2$ and the characteristics of an end point E4 of the second blood vessel of the non-target layer $L_1$ coincide with each other in the example shown in FIG. 4, the second blood vessel extraction unit 83 extracts the second blood vessel, which includes the end point E4, (a thick blood vessel positioned inside a dotted line) from the non-target layer $L_1$. Likewise, since the characteristics of the end point E3 of the second blood vessel of the target layer $L_2$ and the characteristics of an end point E5 of the second blood vessel of the non-target layer $L_3$ coincide with each other, the second blood vessel extraction unit 83 extracts the second blood vessel, which includes the end point E5, from the non-target layer $L_3$.

On the other hand, since the second blood vessel, which includes an end portion coinciding with the characteristics of the end point E2 of the second blood vessel of the target layer $L_2$, is not present in the non-target layers $L_1$ and $L_3$, the second blood vessel extraction unit 83 does not extract a blood vessel from the non-target layer corresponding to the second blood vessel including the end point E2. A case in which a blood vessel is not detected since the blood vessel is thin, a case in which a blood vessel is not detected since a blood flow rate is low, and the like are thought as the reason why the second blood vessel, which coincides with the characteristics of the end point E2 of the second blood vessel of the target layer $L_2$, is not detected in the non-target layer $L_1$ or $L_3$.

Further, in this embodiment, both ends of the second blood vessel, which is detected in the non-target layer $L_3$ and includes the end point E5, are cut in the image of the non-target layer $L_3$ and the second blood vessel includes the other end point E6. In this case, the second blood vessel extraction unit 83 also extracts a second blood vessel, which extends to the fourth layer $L_4$ (non-target layer $L_4$) adjacent to the non-target layer $L_3$, from the non-target layer $L_4$. That is, the second blood vessel extraction unit 83 extracts a second blood vessel, which includes an end point E7 of which the characteristics coincide with the characteristics of the end point E6 of the second blood vessel of the non-target layer $L_3$, from the non-target layer $L_4$.

The special observation image-generation unit 85 generates one image (special observation image), which represents a whole image of the first and second blood vessels, on the basis of the first blood vessels that are extracted from the target layer by the first blood vessel extraction unit 82 and the second blood vessels that are extracted by the second blood vessel extraction unit 83, extend to the non-target layers from the target layer, and are present in the non-target layers. FIG. 4 shows an aspect in which the special observation image showing the blood vessels of the target layer $L_2$ (including the blood vessels of the non-target layers that extend to the non-target layers from the target layer) is generated from four images of the first to fourth layers $L_1$ to $L_4$. The special observation image-generation unit 85 may be adapted to generate a stereoscopic image that includes the first blood vessels of the target layer and the second blood vessels of the non-target layers.

The vascular information calculation unit 90 calculates vascular information on these first and second blood vessels on the basis of the first blood vessels that are extracted from the target layer by the first blood vessel extraction unit 82 and the second blood vessels that are extracted by the second blood vessel extraction unit 83, extend to the non-target layers from the target layer, and are present in the non-target layers.

In a case in which blood vessels extending to the non-target layers from the target layer to be measured of the subject are present as described above, the second blood vessels of the non-target layers, which extend to the non-target layers from the target layer, are also extracted in addition to the first blood vessels of the target layer and vascular information on these first and second blood vessels are calculated. Accordingly, vascular information on the blood vessels of the target layer can be accurately acquired.

Here, the vascular information calculated by the vascular information calculation unit 90 includes at least two of the number of blood vessels, the number of branches of blood vessels, the thickness and length of a blood vessel, an interval between blood vessels, the depth, sinuosity, area, and density of a blood vessel, the concentration of blood in a blood vessel, the oxygen saturation of a blood vessel, the ratio of arteries, the ratio of veins, a travel pattern of blood vessels, or a blood flow rate in a blood vessel.

The number of blood vessels is the number of blood vessels that are extracted by the first blood vessel extraction unit 82 and the second blood vessel extraction unit 83, but blood vessels extending to the non-target layer from the target layer are counted as one blood vessel.

The thickness of a blood vessel (the diameter of a blood vessel) is a distance between the boundary line of a blood vessel and the boundary line of a mucous membrane, and is counted by, for example, counting the number of pixels from the edge of the extracted blood vessel through the blood vessel in the lateral direction of the blood vessel. Accordingly, the thickness of the blood vessel is the number of pixels, but can be converted into the unit of a length, such as "µm", as necessary in a case in which an imaging distance, a focal length, and the like at the time of taking of an endoscope image are already known.

The length of a blood vessel can be calculated from the number of pixels that is counted in the longitudinal direction of the extracted blood vessel.

The interval between blood vessels is the number of pixels that represent a mucous membrane positioned between the edges of the extracted blood vessels.

The depth of a blood vessel can be, for example, considered as the depth of a selected target layer (the depth representing the target layer).

The sinuosity of a blood vessel is vascular information that represents the area of a range where a blood vessel travels while meandering. The sinuosity of a blood vessel is, for example, the area (the number of pixels) of the minimum rectangle that includes the blood vessel and is used to calculate sinuosity. Further, a ratio of the length of a blood vessel to a lineal distance between the starting point and the end point of the blood vessel may be used as the sinuosity of the blood vessel.

The area of a blood vessel is the number of pixels extracted as a blood vessel or a value that is proportional to the number of pixels extracted as a blood vessel.

The density of a blood vessel is a ratio of a blood vessel present in a unit area. A region (for example, a region having a unit area) having a specific size and including pixels, which are used to calculate the density of a blood vessel, substantially at the center thereof is cut out, and a ratio of pixels occupied by the blood vessel to all pixels of this region is calculated. It is possible to calculate the density of a blood vessel by performing this calculation in a region of interest or on all pixels of the entire endoscope image.

The concentration of blood in a blood vessel is vascular information proportional to the amount of hemoglobin included in a blood vessel. Since a ratio (G/R) of the pixel value of a G pixel to the pixel value of an R pixel, which represents a blood vessel, is proportional to the amount of hemoglobin, the concentration of blood can be calculated for every pixel through the calculation of the ratio (G/R).

The oxygen saturation of a blood vessel is the amount of oxygenated hemoglobin with respect to the total amount of hemoglobin (the total amount of oxygenated hemoglobin and reduced hemoglobin). The oxygen saturation can be calculated using the endoscope image of an object to be observed that is taken with light having a specific wavelength range where a difference between the light absorption coefficient of oxygenated hemoglobin and the light absorption coefficient of reduced hemoglobin is large (for example, blue light having a wavelength of about 470±10 nm). Since the pixel values of B pixels of pixels which represent a blood vessel have a correlation to oxygen saturation in a case in which blue light having a wavelength of about 470±10 nm is used, the oxygen saturation of each pixel, which represents a blood vessel, can be calculated using a table in which the pixel values of B pixels are associated with oxygen saturation or the like.

The ratio of arteries is a ratio of the number of pixels of arteries to the number of pixels of all blood vessels. Likewise, the ratio of veins is a ratio of the number of pixels of veins to the number of pixels of all blood vessels. Arteries and veins can be distinguished using oxygen saturation. For example, in a case in which blood vessels of which oxygen saturation is 70% or more are referred to as arteries and blood vessels of which oxygen saturation is lower than 70% are referred to as veins, extracted blood vessels can be classified into arteries and veins. Accordingly, the ratio of arteries and the ratio of veins can be calculated.

The travel pattern of blood vessels is vascular information on the travel direction of blood vessels. The travel pattern of blood vessels is, for example, the average angle (travel direction) of blood vessels with respect to a randomly set reference line, a variance of angles between the blood vessels and a randomly set reference line (a variation in the travel direction), or the like.

The blood flow rate (also referred to as blood flow velocity) in a blood vessel is the number of red blood cells passing per unit time.

Returning to FIG. 2, image data, which is generated by the image processing section 65 (normal observation image-generation unit 71) and represents the normal observation image, is output to the display control unit 66 in a case in which an observation mode is switched to the normal observation mode, and image data, which is generated by the image processing section 65 (special observation image-generation unit 85) and represents the special observation image, is output to the display control unit 66 in a case in which an observation mode is switched to the special observation mode.

The display control unit 66 generates data for display, which allows the display unit 14 to display the normal observation image or the special observation image, from the input image data, outputs the generated data for display to the display unit 14, and allows the display unit 14 to display an image for display.

Further, in a case in which the vascular information is calculated by the vascular information calculation unit 90, the image processing section 65 outputs the calculated vascular information to the display control unit 66 and/or the storage unit 67. In a case in which the vascular information is input to the display control unit 66 from the image processing section 65, the display control unit 66 allows the display unit 14 to display the vascular information. Furthermore, in a case in which the vascular information is input to the storage unit 67 from the image processing section 65, it is preferable that the vascular information is recorded in association with information on the target layer.

In the above-mentioned embodiments, the processor control unit 61 sequentially sets the image acquisition conditions corresponding to the taking of the images of the first to fourth layers $L_1$ to $L_4$, sequentially takes the images of all of the first to fourth layers $L_1$ to $L_4$, and stores the images of all of the layers in the storage unit 67 in advance. However, the invention is not limited thereto, and the processor control unit 61 may acquire the images of non-target layers, which are adjacent to the target layer, again by the taking of an image in a case in which the processor control unit 61 acquires the image of the target layer by the taking of an image, analyzes the acquired image of the target layer, and determines that the second blood vessels are present in the target layer.

[Vascular Information Acquisition Method]

Next, a vascular information acquisition method according to the invention will be described.

<First Embodiment of Vascular Information Acquisition Method>

Figure 5:
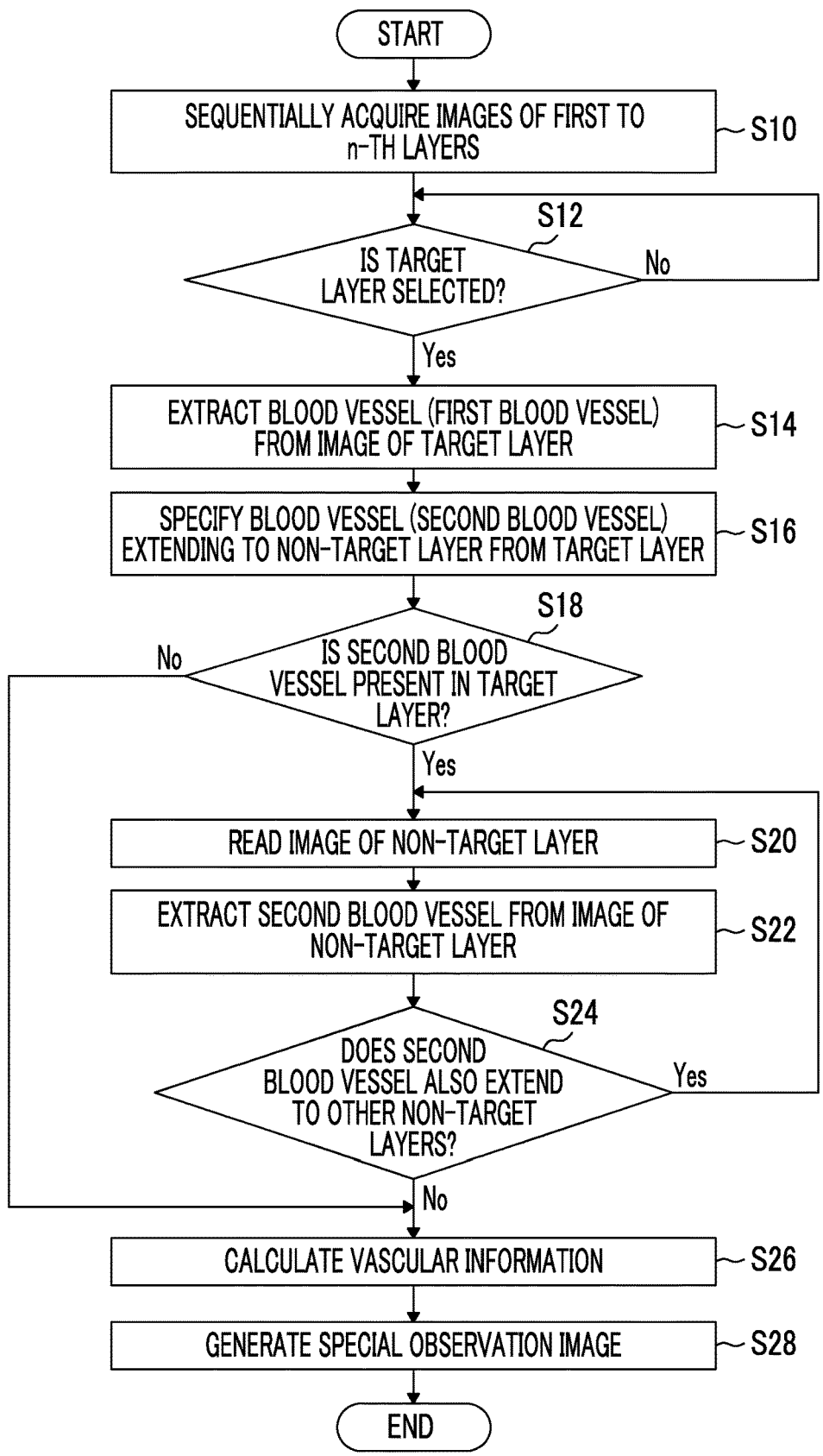
FIG. 5 is a flowchart showing a first embodiment of a vascular information acquisition method according to the invention.

FIG. 5 is a flowchart showing a first embodiment of the vascular information acquisition method according to the invention.

As shown in FIG. 5, in the case of the vascular information acquisition mode, the processor control unit 61 controls the light source device 12 and the endoscope 11 and sequentially acquires the images of the first to n-th layers as the endoscope images of a subject (Step S10). Since the plurality of layers, which have different depths, of the subject are four layers in the case of this embodiment, n is 4. Further, the images of the respective layers can be acquired through the taking of images while image acquisition conditions, such as the wavelength of illumination light, are sequentially switched for every frame. The acquired respective images are temporarily stored in the storage unit 67 or a buffer memory.

Subsequently, the processor control unit 61 determines whether or not a specific layer (target layer) from which vascular information is desired to be acquired is selected among the first to n-th layers (Step S12). This determination can be performed on the basis of the operation of the target layer selector of the processor operation unit 13*a*.

If the target layer is selected (in the case of "Yes"), an image, which is taken so as to correspond to the target layer, is read from the storage unit 67, the read image of the target layer is analyzed, and blood vessels (first blood vessels) are extracted from the image of the target layer (Step S14).

Subsequently, blood vessels (second blood vessels), which extend to the non-target layers from the target layer, are specified among the extracted first blood vessels (Step S16). The second blood vessels, which extend to the non-target layers from the target layer, can be specified through the detection of blood vessels that are cut in the image.

Next, it is determined whether or not the second blood vessels, which extend to the non-target layers from the target layer, are present (Step S18). If the second blood vessels, which extend to the non-target layers from the target layer, are present (in the case of "Yes"), the images of the non-target layers adjacent to the target layer are read from the storage unit 67 (Step S20). Subsequently, the read images of the non-target layers are analyzed, and only the specified second blood vessels are extracted from the images of the non-target layers (Step S22). Only the second blood vessels, which are specified from the images of the non-target layers, can be extracted through the evaluation of the connection of the end points of the cut blood vessels.

Subsequently, it is determined whether or not the second blood vessels also extend to non-target layers further adjacent to the non-target layers adjacent to the target layer (Step S24). If the second blood vessels extend to the non-target layers (in the case of "Yes"), processing proceeds to Step S20 and the images of the non-target layers to which the second blood vessels further extend are acquired and the second blood vessels are extracted from the non-target layers.

If it is determined that the second blood vessels, which extend to the non-target layers from the target layer, are not present in Step S18 (in the case of "No") or if it is determined that the second blood vessels, which extend to the other non-target layers from the non-target layers, are not present in Step S24 (in the case of "No"), vascular information is calculated on the basis of the extracted blood vessels (Step S26).

Further, one image (special observation image) in which the extracted first and second blood vessels are integrated with each other is generated (Step S28).

<Second Embodiment of Vascular Information Acquisition Method>

Figure 6:
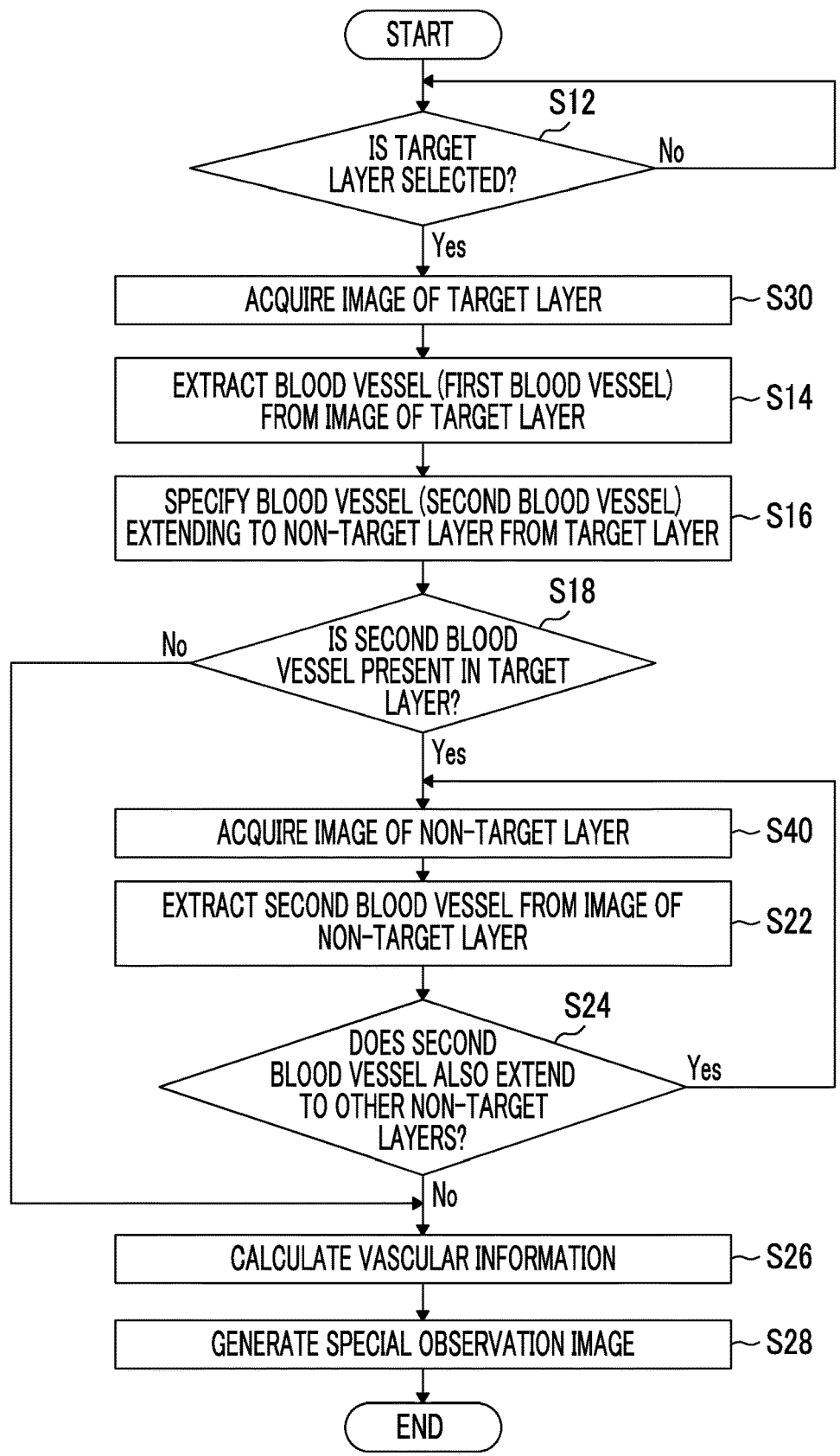
FIG. 6 is a flowchart showing a second embodiment of the vascular information acquisition method according to the invention.

FIG. 6 is a flowchart showing a second embodiment of the vascular information acquisition method according to the invention. Steps common to the first embodiment shown in FIG. 5 are denoted by the same step numbers as those of the first embodiment, and the detailed description thereof will be omitted.

In the first embodiment, after the images of all of the first to n-th layers are acquired as the endoscope images of a subject and the images of all layers are stored in the storage unit 67, the stored images of the respective layers are analyzed so that processing for extracting the blood vessels of the target layer and the non-target layers and the like are performed. However, the second embodiment is different from the first embodiment in that the taking of the images of the non-target layers and the like are performed as necessary after the image of a target layer is acquired.

As shown in FIG. 6, in the case of the vascular information acquisition mode, the processor control unit 61 determines whether or not a specific layer (target layer) from which vascular information is desired to be acquired is selected (Step S12).

If the target layer is selected, the processor control unit 61 takes the image of the selected target layer and acquires the image of the target layer (Step S30).

After processing for extracting the first blood vessels from the acquired image of the target layer (Step S14) and processing for specifying the second blood vessels extending to the non-target layers from the target layer (Step S16) are performed, it is determined whether or not the second blood vessels extending to the non-target layers from the target layer are present (Step S18).

Then, if the second blood vessels extending to the non-target layers from the target layer are present (in the case of "Yes"), the processor control unit 61 takes the images of the non-target layers adjacent to the target layer and acquires the images of the non-target layers (Step S40).

Next, the images of the non-target layers, which are acquired in Step S40, are analyzed and only the second blood vessels, which are specified from the images of the non-target layers, are extracted (Step S22). Subsequently, it is determined whether or not the second blood vessels also extend to non-target layers further adjacent to the non-target layers adjacent to the target layer (Step S24). If the second blood vessels extend to the non-target layers (in the case of "Yes"), processing proceeds to Step S40 and the images of the non-target layers to which the second blood vessels extend are taken and new images of non-target layers are acquired.

In the first embodiment, images do not need to be taken again in a case in which the selection of the target layer is changed to temporarily acquire the images of all the layers. On the other hand, in the second embodiment, processing time can be shortened since the images of unnecessary non-target layers are not taken in a case in which blood vessels extending to the non-target layers from the target layer are not present.

[Others]

In this embodiment, in a case in which the blood vessels (second blood vessels) extending to the non-target layers from the target layer are present, second blood vessels are traced and extracted over all of the non-target layers other than the target layer as long as the second blood vessels are present. However, the invention is not limited thereto, and determination values may be set and the extraction (tracing) of the second blood vessels extending to the non-target layers may be stopped on the basis of the set determination values.

Here, the determination values are information that is determined so as to correspond to the vascular information on the second blood vessels, and the second blood vessel extraction unit 83 continues or stops the extraction of the second blood vessels according to whether or not the vascular information on the second blood vessels satisfies the determined information.

The determination values are depth information corresponding to the depths of the blood vessels, and the second blood vessel extraction unit 83 stops the extraction of the second blood vessels in a case in which the depth information is set and the depths of the second blood vessels reach depths indicated by the depth information. For example, depth information corresponding to the non-target layers adjacent to the target layer is set, so that the tracing of the second blood vessels cannot be performed on other non-target layers further adjacent to the non-target layers. Further, the extraction of the second blood vessel may be stopped in a case in which the second blood vessel reaches a preset depth.

Furthermore, in a case in which the thicknesses of the second blood vessels are changed, a case in which the second blood vessels are branched, or a case in which a range from which the blood vessels are extracted is limited, the extraction of the second blood vessels extending to the non-target layers can be stopped according to these conditions (determination values). For example, since the thickness of the blood vessel is changed in a case in which one second blood vessel branches into two blood vessels, this is extracted by image analysis and the extraction of the second blood vessels extending to the non-target layers from the target layer may be stopped at this timing.

Further, the vascular information acquisition device is not limited to the processor device 13, and may be formed of an external computer. In this case, the vascular information acquisition device may acquire the images of a plurality of layers, which have different depths, of a subject from the storage unit 67 of the processor device 13; and may be connected to the processor device 13 through a network and may acquire the images of a plurality of layers, which have different depths, of a subject from a server in which the images of the plurality of layers, which have different depths, of a subject are stored.

Furthermore, it goes without saying that the invention is not limited to the above-mentioned embodiments and has various modifications without departing from the scope of the invention.

EXPLANATION OF REFERENCES

1: blood vessel
10: endoscope system
11: endoscope
12: light source device
12a: light source operation unit
13: processor device
13a: processor operation unit
14: display unit
16: insertion part
16a: insertion-part-distal end portion
16b: bendable portion
16c: flexible tube portion
17: hand operation unit
18: universal cord
21: angle knob
22: operation button
23: forceps inlet
25a: connector part
25b: connector part
31: light source control unit
32: light source unit
32a: V-LED
32b: B-LED
32c: G-LED
32d: R-LED
40: light guide
42: illumination lens
44: objective lens
45: imaging element
46: endoscope operation unit
47: endoscope control unit
48: ROM
61: processor control unit
62: ROM
65: image processing section
66: display control unit
67: storage unit
70: normal observation image-processing unit
71: normal observation image-generation unit
80: special observation image-processing unit
81: image acquisition unit
82: first blood vessel extraction unit
83: second blood vessel extraction unit
84: blood vessel specification unit
85: special observation image-generation unit
90: vascular information calculation unit
E1 to E7: end point
$L_1$ to $L_4$: first to fourth layers
$L_1$, $L_3$, $L_4$: non-target layer
$L_2$: target layer
S10 to S40: Step

What is claimed is:

1. A vascular information acquisition device comprising:
a processor configured to acquire images of a plurality of layers, which have different depths, of a subject;
select one layer of the plurality of layers as a target layer;
analyze the image of the selected target layer and extracts a first blood vessel from the image of the target layer;
specify a second blood vessel extending to a non-target layer, which is a layer other than the target layer among the plurality of layers, from the selected target layer;
analyze the image of the non-target layer in which the specified second blood vessel is present and extracts the specified second blood vessel from the image of the non-target layer; and
calculate vascular information on the first and/or second blood vessels extracted by the processor,
wherein the processor is configured to calculate a plurality of pieces of the vascular information including at least two of the number of blood vessels, the number of branches of blood vessels, thickness and length of a blood vessel, an interval between blood vessels, depth, sinuosity, area, and density of a blood vessel, concentration of blood in a blood vessel, an oxygen saturation of a blood vessel, a ratio of arteries, a ratio of veins, a travel pattern of blood vessels, or a blood flow rate in a blood vessel, wherein the oxygen saturation of the blood vessel is calculated by using a blue light having a wavelength of about 470±10 nm, wherein the processor stops the extraction of the second blood vessel, which extends to the non-target layer, on the basis of a determination value, wherein the determination value is depth information corresponding to a depth of a blood vessel, and the processor stops the extraction of the second blood vessel in a case in which a depth of the second blood vessel reaches a depth indicated by the depth information.

2. The vascular information acquisition device according to claim 1, further comprising:

the processor configured to allow a display to display the first and second blood vessels extracted by the processor.

3. The vascular information acquisition device according to claim 2, wherein in a case in which the second blood vessel also extends to a non-target layer different from the non-target layer, the processor also performs the extraction of the second blood vessel on the different non-target layer.

4. The vascular information acquisition device according to claim 2, wherein the processor stops the extraction of the second blood vessel, which extends to the non-target layer, on the basis of a determination value.

5. The vascular information acquisition device according to claim 1, wherein in a case in which the second blood vessel also extends to a non-target layer different from the non-target layer, the processor also performs the extraction of the second blood vessel on the different non-target layer.

6. The vascular information acquisition device according to claim 1, wherein the determination value is information that is determined so as to correspond to the vascular information on the second blood vessel, and the processor determines whether to continue or stop the extraction of the second blood vessel according to whether or not the vascular information on the second blood vessel satisfies the determined information.

7. An endoscope system comprising:

the vascular information acquisitiondevice according to claim 1, further comprising the processor configured to include a plurality of image acquisition conditions corresponding to the taking of images of a plurality of layers, which have different depths, of a subject, and sets any image acquisition condition of the plurality of image acquisition conditions; and an endoscope that images the subject under the image acquisition condition set by the processor and acquires an image of a layer, which has a depth corresponding to the set image acquisition condition, among the plurality of layers, wherein the processor acquires images of the plurality of layers, which have different depths, of the subject from the endoscope.

8. The endoscope system according to claim 7, wherein the processor sequentially selects one image acquisition condition among the plurality of image acquisition conditions and sets the selected image acquisition condition, and the endoscope images the subject whenever the image acquisition condition is set by the processor, and sequentially acquires an image of a layer, which has a depth corresponding to the set image acquisition condition.

9. The endoscope system according to claim 7, wherein the processor sets an image acquisition condition corresponding to an image of the selected target layer in a case in which the target layer is selected by the processor, and sets an image acquisition condition corresponding to an image of a non-target layer adjacent to the target layer in a case in which the second blood vessel is specified by the processor, and the endoscope images the subject whenever the image acquisition condition is set by the processor, and acquires an image of a layer, which has a depth corresponding to the set image acquisition condition.

10. A vascular information acquisition method comprising:

acquiring images of a plurality of layers, which have different depths, of a subject;

selecting one layer of the plurality of layers as a target layer;

analyzing an image of the selected target layer and extracting a first blood vessel from the image of the target layer;

specifying a second blood vessel extending to a non-target layer, which is a layer other than the target layer among the plurality of layers, from the selected target layer;

analyzing the image of the non-target layer in which the specified second blood vessel is present and extracting the specified second blood vessel from the image of the non-target layer; and calculating vascular information on the extracted first and/or second blood vessels, wherein a plurality of pieces of the vascular information including at least two of the number of blood vessels, the number of branches of blood vessels, thickness and length of a blood vessel, an interval between blood vessels, a depth of a blood vessel based on a mucous membrane, sinuosity, area, and density of a blood vessel, concentration of blood in a blood vessel, an oxygen saturation of a blood vessel, a ratio of arteries, a ratio of veins, a travel pattern of blood vessels, or a blood flow rate in a blood vessel are calculated by calculating the vascular information, wherein the oxygen saturation of the blood vessel is calculated by using a blue light having a wavelength of about 470±10 nm, wherein the extraction of the second blood vessel, which extends to the non-target layer, is stopped on the basis of a determination value, wherein the determination value is depth information corresponding to a depth of a blood vessel, and the extraction of the second blood vessel in a case in which a depth of the second blood vessel reaches a depth indicated by the depth information is stopped.

* * * * *